United States Patent [19]

Grooters

[11] Patent Number: 4,960,424
[45] Date of Patent: Oct. 2, 1990

[54] METHOD OF REPLACING A DEFECTIVE ATRIO-VENTRICULAR VALVE WITH A TOTAL ATRIO-VENTRICULAR VALVE BIOPROSTHESIS

[76] Inventor: Ronald K. Grooters, 3300 Fuller Rd., West Des Moines, Iowa 50265

[21] Appl. No.: 214,128

[22] Filed: Jun. 30, 1988

[51] Int. Cl.$^5$ .............................................. A61F 2/24
[52] U.S. Cl. .................................................... 623/2
[58] Field of Search .............. 623/2, 1, 3; 128/334 R

[56] References Cited

U.S. PATENT DOCUMENTS

| | | | |
|---|---|---|---|
| 2,127,903 | 8/1938 | Bowen | 623/1 |
| 3,671,979 | 6/1972 | Moulopoulos | 3/1 |
| 4,056,854 | 11/1977 | Boretos et al. | 3/1.5 |
| 4,261,342 | 4/1981 | Duo | 128/1 R |
| 4,275,469 | 6/1981 | Gabbay | 3/1.5 |
| 4,400,833 | 8/1983 | Kurland | 128/334 R |
| 4,441,215 | 4/1984 | Kaster | 128/334 R |
| 4,469,101 | 9/1984 | Coleman et al. | 128/334 R |
| 4,683,883 | 8/1987 | Martin | 128/303 R |
| 4,790,844 | 12/1988 | Ovil | 623/2 |

FOREIGN PATENT DOCUMENTS 782808 11/1980 U.S.S.R. .

Primary Examiner—Randall L. Green
Assistant Examiner—Stephanie L. Iantorno
Attorney, Agent, or Firm—Zarley McKee, Thomte, Voorhees & Sease

[57] ABSTRACT

The method of replacing a defective atrio-ventricular valve in a patient's heart with a tissue atrio-ventricular valve bioprosthesis is provided. The replacement atrio-ventricular valve from the donor heart includes an annulus, a plurality of chordae, and papillary muscles attached thereto. The surgical operation includes removal of the defective valve from the patient's heart, and the insertion of each papillary muscle of the replacement valve longitudinally into a corresponding papillary muscle in the patient's heart. The papillary muscles of the replacement valve are secured in position within the patient's heart and the annulus of the replacement valve is secured to the annulus of the patient's heart. An introducer is utilized for inserting the papillary muscles of the replacement valve into the papillary muscle of the patient's heart, using the Seldinger technique.

21 Claims, 2 Drawing Sheets

U.S. Patent  Oct. 2, 1990  Sheet 1 of 2  4,960,424
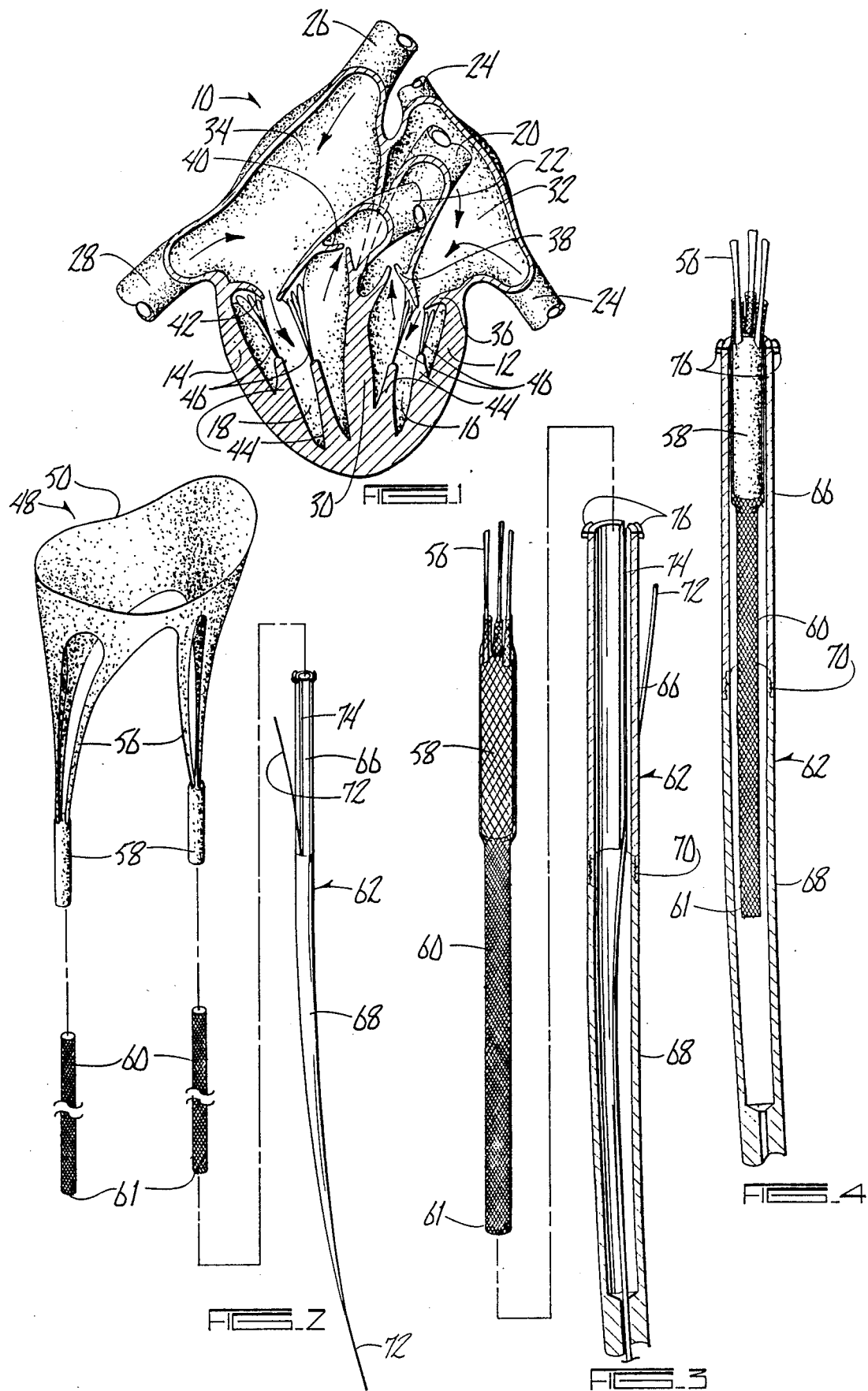

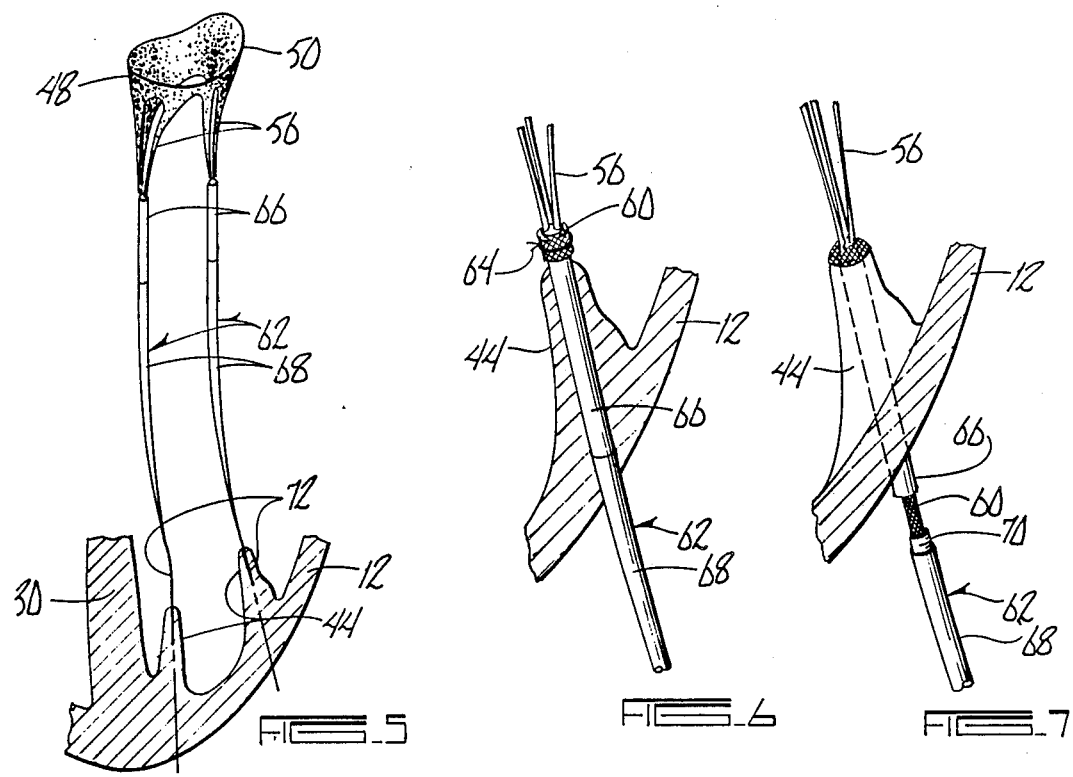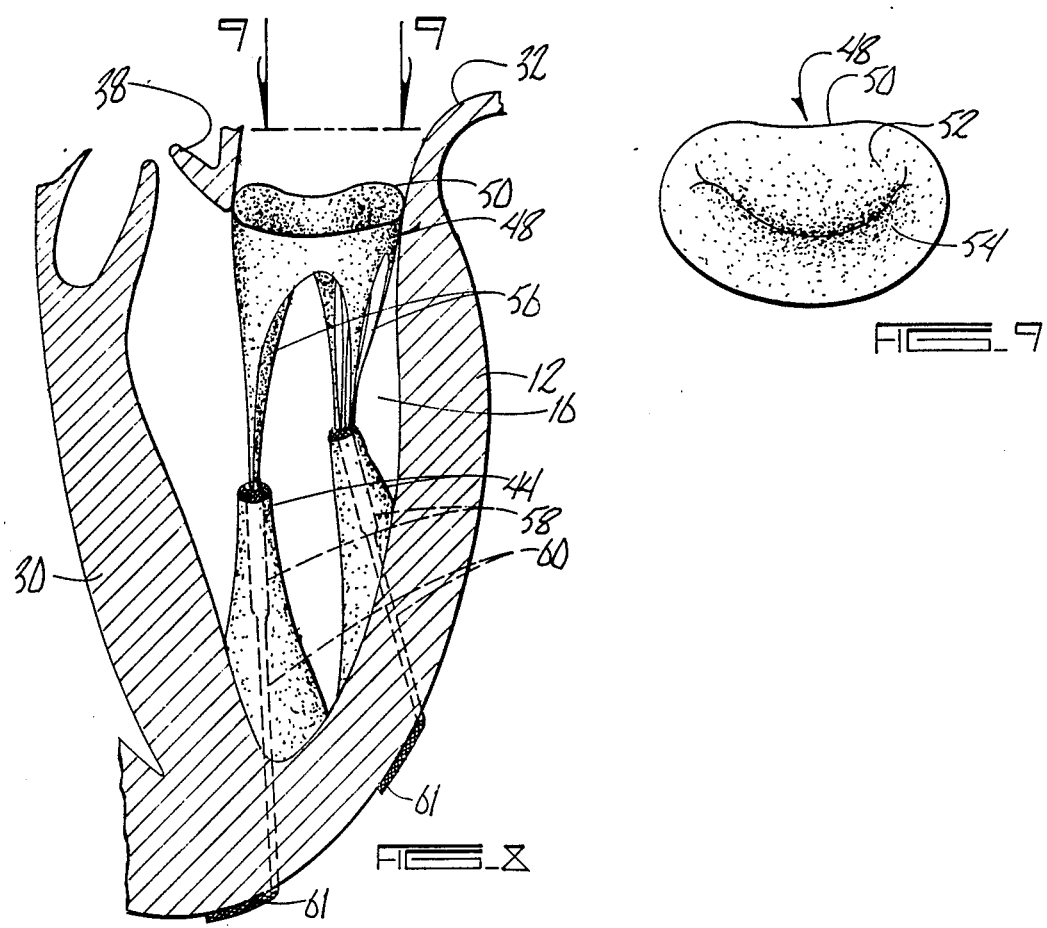

METHOD OF REPLACING A DEFECTIVE ATRIO-VENTRICULAR VALVE WITH A TOTAL ATRIO-VENTRICULAR VALVE BIOPROSTHESIS

BACKGROUND OF THE INVENTION

When an atrio-ventricular valve of a human's heart becomes defective, it has been customary to replace the valve with a man-made mechanical valve or a porcine bioprosthetic valve. While these replacement valves normally prolong the patient's life, there are complications involved. For example, ventricular dilatation is common after mitral valve replacement since the chordae of the replacement valve are detached from the papillary muscle and ventricular wall, thus allowing distention of the left ventricle. Also, with tissue valves such as the porcine bioprosthesis valve, the cusps normally are attached to artificial struts and a sewing ring, which in turn are sutured to the annulus of the removed valve. These struts may result in ventricular perforation or injury to the bioprosthetic valve cusps during insertion. Furthermore, since the bioprosthetic valve is attached to struts and a large sewing ring, the use of such valve causes post operative pressure gradients and therefore cannot be used in situations requiring use of a small valve. Thus, the function of the patient's heart is not maximized by the use of artificial or bioprosthetic valves in small valve replacement situations.

Therefore, the primary objective of the present invention is the provision of a total atrio-ventricular valve replacement using all the structure of an atrio-ventricular valve as a prosthesis.

Another objective of the present invention is the provision of an atrio-ventricular valve bioprosthesis which preserves the functioning aspects of the atrio-ventricular valve, including the atrial wall for contraction of the annulus, the mobility of the annulus, the valve leaflets, the chordae tendonae, the papillary muscles, and the ventricular wall.

A further objective of the present invention is the provision of a method for replacing a defective atrio-ventricular valve in a human patient which decreases thrombotic complications and minimizes post operative gradients across the replacement valve.

Yet another objective of the present invention is an atrio-ventricular valve bioprosthesis which preserves and restores the ventricle size and configuration so as to prevent ventricular dilatation.

Still another objective of the present invention is the provision of a non-strutted atrio-ventricular valve replacement, which eliminates ventricular perforation and suture injury.

A further objective of the present invention is a method of replacing a defective atrio-ventricular valve with a tissue atrio-ventricular valve configuration matching that of the recipient heart.

Still a further objective of the present invention is the provision of an introducer device for installing a total atrio-ventricular valve prosthesis.

These and other objectives will become apparent from the following description of the invention.

SUMMARY OF THE INVENTION

The invention concerns a method of replacing a defective atrio-ventricular valve in the heart of a patient with a replacement tissue atrio-ventricular valve from a donor heart. This total atrio-ventricular valve replacement contemplates use of a porcine atrio-ventricular valve or a atrio-ventricular valve from a donor human. Preferably, the atrio-ventricular valve bioprosthesis closely matches the defective atrio-ventricular valve of the patient in size and configuration.

The surgical technique involves removing the defective valve from the patient's heart and replacing it with a tissue atrio-ventricular valve having an annulus, a plurality of chordae, and papillary muscles attached thereto. Initially, the diameter of the papillary muscles of the replacement valve is reduced by removing the muscle tissue and leaving the endocardial component. The remaining papillary muscle of the replacement valve is then inserted into a DACRON mesh membrane which has an upper end surrounding the chordae and a lower end which extends beyond the distal end of the papillary muscles. The mesh material and covered papillary muscle is positioned within an introducer for the surgical operation.

In the surgical operation, the defective atrio-ventricular valve is removed from the patient and the introducer with the replacement atrio-ventricular valve secured thereto is inserted longitudinally through the papillary muscles of the patient's heart using the Seldinger technique. The lower end of the introducer which extends through the heart wall is removed for access to the mesh material, which also projects beyond the heart wall. After the valve is positioned in the desired location, it is sutured to the exterior of the heart wall and the papillary muscles of the recipient heart. The annulus of the replacement valve is sutured to the annulus of the recipient heart. The upper portion of the introducer is withdrawn into the heart and peeled from the mesh material by means of a slit in the introducer.

BRIEF DESCRIPTION OF THE DRAWING

FIG. 1 is a schematic sectional view of a human heart.

FIG. 2 is a schematic exploded view of the replacement valve and introducer.

FIG. 3 is an enlarged partially exploded view of a portion of the replacement valve and a portion of the introducer.

FIG. 4 is a partial sectional view showing the position of the papillary muscle of the replacement valve and the surrounding mesh material within the introducer.

FIGS. 5-7 are schematic views showing a sequence of steps involved in the valve replacement technique.

FIG. 8 is an enlarged sectional view showing the replacement valve in place within the recipient heart.

FIG. 9 is a view taken along lines 9—9 of FIG. 8.

DETAILED DESCRIPTION OF THE DRAWINGS

Reference numeral 10 generally designates a recipient heart, which is schematically shown in FIG. 1. The heart generally includes the anterior wall 12, the posterior wall 14 and left and right ventricles 16 and 18, respectively. The major arteries and veins of the heart are also shown in FIG. 1, including the aorta 20, the pulmonary artery 22, the pulmonary veins 24, and the superior and inferior vena cava 26 and 28, respectively. The septum 30 divides the left and right ventricles. The left and right atriums are designated by the reference numerals 32 and 34, respectively. Various valves within the heart are also shown, including the bicuspid mitral valve 36, the aortic valve 38, and pulmonary valve 40, and the tricuspid valve 42. Papillary muscles are designated by the reference numeral 44, while the chordae tendonae are designated by the reference numeral 46.

The replacement atrio-ventricular valve 48 is generally shown in FIG. 2. This replacement valve is a tissue valve from a pig or another human, and includes an annulus 50 and anterior and posterior leaflets 52 and 54, respectively, as seen in FIG. 9. Replacement valve 48 also includes chordae tendonae 56 and papillary muscle 58. Preferably, papillary muscles 58 are reduced in diameter to approximately 2-3 millimeters by removing the interior muscle and leaving the endocardial component.

The papillary muscles 58 of replacement valve 48 are inserted into a membrane 60, such as a DACRON mesh material, as best seen in FIGS. 3 and 4. For security, the mesh material can be woven around chordae 56. Alternatively, membrane 60 may extend over the upper end of an introducer 62, described below, and be secured thereto by a string or wire 64, as seen in FIG. 6. Membrane 60 extends beyond the distal end of the papillary muscles.

The papillary muscle 58 with the surrounding membrane 60 is positioned within introducer 62, as shown in FIG. 4. Introducer 62 includes an upper section 66 and a lower section 68 which are connected together at their adjacent ends. This connection can be made by any convenient means, such as mating threads 70, as best seen in FIGS. 3 and 4. Other connection means may be employed, such as a friction press fit. As seen in FIG. 4, membrane 60 extends into lower section 68 of introducer 62.

In the surgical operation, the defective heart valve is removed from recipient heart 10 by cutting the chordae 46 adjacent the papillary muscles 44 and cutting the annulus of the defective valve.

The introducer is inserted longitudinally into the papillary muscle 44 and through the wall of the recipient heart, using the Seldinger technique. Basically, that technique involves inserting a needle (not shown) through the papillary muscle and wall of the recipient heart, and inserting a wire 72 through the needle. The needle is then removed and the introducer 62 is guided along the wire 72, which extends through the lower section 68 of the introducer and emerges at the joint between the upper and lower sections.

After the introducer is in the position shown in FIG. 7 wherein the upper section 66 protrudes from the heart wall, the lower section 68 of the introducer is removed, thereby exposing the end 61 of membrane 60. After the replacement valve 48 is positioned within heart 10 as desired, ends 61 of membrane 60 are secured with sutures to the exterior of the heart wall. Membrane 60 is also secured with sutures to the papillary muscle 44. Annulus 50 of replacement valve 48 is sutured into position, as shown in FIG. 8. To complete the operation, string or wire 64 is removed and upper section 66 of introducer 62 is drawn into the ventricle and peeled from the chordae 56 by means of a slit 74 extending along the length of uppe section 66. Some form of a gripping means, such as handles 76 may be provided on the upper end of section 66 to facilitate the removal thereof.

The drawings illustrate replacement of mitral valve 16. However, it is understood that the described procedure may be utilized to replace any of the atrio-ventricular valves in the heart. Also, it is understood that the bioprosthesis may be monocuspid or bicuspid without true departing from the scope of the present invention.

By using a tissue atrio-ventricular valve bioprosthesis according to the present invention, rather than a standard tissue valve or mechanical valve, many advantages are obtained. More particularly, the method of the present invention minimizes or eliminates the ventricular dilatation and preserves or restores the ventricle size and configuration. Also, since the valve replacement method of the present invention does not utilize struts, as in prior art methods, the complications of ventricular perforation and suture injury of the valve cusps at the attachment to the struts is eliminated. Furthermore, thrombotic complications are decreased and post operative gradients across the replacement valve are minimized. Thus, the structural integrity of the replacement valve and the recipient heart are maintained.

Those skilled in the art recognize that the compatibility of transplant valves or organs is necessary for success of the operation. Fixing of the replacement valve, as with other transplant organs, is a known prerequisite to the surgery. The preparation of the replacement valve for compatibility with the patient's heart, apart from the valve replacement method, is not a part of the present invention.

From the foregoing, it can be seen that the present invention accomplishes at least all of the stated objectives.

What is claimed is:

1. A method of replacing a defective atrio-ventricular valve in a heart of a patient with a replacement atrio-ventricular valve from, a donor heart, the replacement atrio-ventricular valve having an annulus, a plurality of chordae and papillary muscles attached thereto, and an elongated membrane extending from each papillary muscle, the method comprising:
removing the defective valve from the patient's heart;
inserting each elongated membrane of the replacement valve longitudinally through a papillary muscle of the patient's heart so that the membrane extends through the heart wall of the patient's heart;
securing the annulus of the replacement valve to the annulus of the patient's heart; and
securing the elongated membranes of the replacement valve to the exterior of the heart wall of the patient.

2. The method of claim 1 further comprising reducing the diameter of the papillary muscle of the replacement valve prior to insertion into the papillary muscle of the patient's heart.

3. The method of claim 2 wherein the diameter of the papillary muscle of the replacement valve is reduced by removing interior muscle thereof.

4. The method of claim 1 wherein the securing of the membrane is with sutures.

5. The method of claim 1 further comprising temporarily securing the membrane and papillary muscle of the replacement valve in an elongated introducer means, and inserting the introducer means longitudinally through the papillary muscle of the patient's heart and through the wall of the patient's heart.

6. The method of claim 5 wherein the introducer means is inserted through the papillary muscle and wall of the patient's heart by the Seldinger technique.

7. The method of claim 5 further comprising removing the introducer means from the patient's heart.

8. The method of claim 7 wherein the introducer means includes separable upper and lower sections, the lower section being removed from the patient's heart by passing through the wall thereof, and the upper section being removed from the patient's heart by withdrawal from the papillary muscle of the patient's heart.

9. The method of claim 8 wherein the upper section of the introducer means is split along its length and the upper section is spread open for removal from the membrane surrounding the papillary muscle of the replacement valve.

10. The method of claim 1 further comprising adjusting the position of the chordae and papillary muscles of the replacement valve within the patient's heart prior to securement of the elongated membranes to the heart wall.

11. A method of replacing a defective atrio-ventricular valve in a heart of a patient with a replacement valve having an annulus and a plurality of elongated members extending therefrom, the method comprising:
removing the defective valve from the patient's heart;
inserting each elongated member of the replacement valve longitudinally through a papillary muscle and the heart wall of the patient's heart;
securing the annulus of the replacement valve to the annulus of the patient's heart; and
securing the elongated members of the replacement valve to the exterior of the heart wall of the patient.

12. The method of claim 11 wherein further comprising adjusting the lengths of the elongated members within the patient's heart prior to securement to the heart wall.

13. The method of claim 11 wherein the elongated members includes choradae and papillary muscles extending from the annulus of the valve, with the securing membrane extending from each of the papillary muscles, the securing membrane being attached to the exterior heart wall of the patient.

14. The method of claim 13 further comprising extending the papillary muscles of the replacement valve into the papillary muscles of the patient's heart.

15. The method of claim 11 wherein the elongated members are secured to the heart with sutures.

16. The method of claim 11 further comprising temporarily securing the elongated member of the replacement valve in an elongated introducer means, and inserting the introducer means longitudinally through the papillary muscle of the patient's heart and through the wall of the patient's heart.

17. The method of claim 16 wherein the introducer means is inserted through the papillary muscle and wall of the patient's heart by guiding he introducer along a wire previously inserted through the papillary muscle and wall of the patient's heart.

18. The method of claim 16 further comprising removing the introducer means from the patient's heart.

19. The method of claim 18 wherein the introducer means includes separable upper and lower sections, the lower section being removed from the patient's heart by passing through the wall thereof, and the upper section being removed from the patient's heart by withdrawal from the papillary muscle of the patient's heart.

20. The method of claim 19 wherein the upper section of the introducer means is split along its length and the upper section is spread open for removal from the elongated member of the replacement valve.

21. The method of claim 11 wherein the replacement valve is fixed prior to removing the defective valve from the patient's heart so as to enhance compatibility of the replacement valve with the patient's heart.

* * * * *